United States Patent [19]

Becher

[11] Patent Number: 5,236,421
[45] Date of Patent: Aug. 17, 1993

[54] FIXING SYSTEM FOR FASTENING CATHETERS, CANNULAS OR THE LIKE TO THE SKIN SURFACE AND PROCESS FOR THE STERILE FASTENING THEREOF

[75] Inventor: Frank Becher, Koblenz, Fed. Rep. of Germany

[73] Assignee: LTS Lohmann Therapie-Systeme GmbH & Co. KG, Neuwied, Fed. Rep. of Germany

[21] Appl. No.: 979,412

[22] Filed: Nov. 19, 1992

Related U.S. Application Data

[63] Continuation of Ser. No. 763,884, Sep. 20, 1991, abandoned, which is a continuation of Ser. No. 632,587, Dec. 21, 1990, abandoned, which is a continuation of Ser. No. 155,712, Mar. 7, 1988, filed as PCT/DE87/00240, May 26, 1987, abandoned.

[30] Foreign Application Priority Data

May 28, 1986 [DE] Fed. Rep. of Germany ....... 3617882
Dec. 22, 1986 [DE] Fed. Rep. of Germany ....... 3643985
Apr. 16, 1987 [DE] Fed. Rep. of Germany ....... 3713114

[51] Int. Cl.⁵ .............................................. A61M 5/32
[52] U.S. Cl. ...................................... 604/180; 602/54
[58] Field of Search .................. 128/743, 887–888, 128/DIG. 26; 604/174, 177–180, 289–290, 304–307; 602/54

[56] References Cited

U.S. PATENT DOCUMENTS

| | | | |
|---|---|---|---|
| 3,026,874 | 3/1962 | Stevens | 128/888 X |
| 3,367,332 | 2/1968 | Groves | 128/888 X |
| 3,612,265 | 10/1971 | Dickerson . | |
| 3,683,911 | 8/1972 | McCormick | 604/180 |
| 3,782,377 | 1/1974 | Rychlik | 604/180 X |
| 3,918,446 | 11/1975 | Buttaravoli . | |
| 4,122,857 | 10/1978 | Haerr | 604/180 |
| 4,324,237 | 4/1982 | Buttaravoli | 604/180 |
| 4,333,468 | 6/1982 | Geist | 604/180 |
| 4,614,183 | 9/1986 | McCracken et al. | 604/180 X |
| 4,678,462 | 7/1987 | Vaillancourt | 604/180 |
| 4,743,232 | 5/1988 | Kruger | 604/180 |

FOREIGN PATENT DOCUMENTS

| | | | |
|---|---|---|---|
| 3129931 | 2/1983 | Fed. Rep. of Germany | 604/180 |
| 0148560 | 8/1985 | Japan | 604/174 |
| 2057269 | 4/1981 | United Kingdom | 604/174 |

*Primary Examiner*—Lee S. Cohen
*Assistant Examiner*—John P. Lacyk
*Attorney, Agent, or Firm*—Kalish & Gilster

[57] ABSTRACT

The invention relates to a fixing system for fixing catheters, cannulas, etc. with a skin film (3) coated with a skin adhesion layer (2) and having a cover film (1) and an overplaster (6) finished with a pressure sensitive adhesive layer (5) adhering to the skin film and having an overplaster cover layer (4), as well as to a process for the sterile fastening of a cannula to the skin with the following steps: application of a bacteria-tight skin film with skin adhesion layer to the skin in the insertion region of the cannula, passing the cannula through the skin film, applying an adhesive forming an elastic, bacteria-tight film adhering to the skin film region surrounding the insertion point and the cannula portion projecting out of the skin and sticking the overplaster over the cannula.

20 Claims, 3 Drawing Sheets

FIXING SYSTEM FOR FASTENING CATHETERS, CANNULAS OR THE LIKE TO THE SKIN SURFACE AND PROCESS FOR THE STERILE FASTENING THEREOF

This application is a continuation of Ser. No. 07/763884, filed Sep. 20, 1991 now abandoned; which is a continuation of Ser. No. 07/632587, filed Dec. 21, 1990 now abandoned; which is a continuation of Ser. No. 07/155712, filed Mar. 07, 1988, filed as PCT/DE87/00240, May 26, 1987, now abandoned.

BACKGROUND OF THE INVENTION

The invention relates to a fixing system for fastening cannulas, catheters, etc. to the skin, as well as to a process for the sterile fastening of a cannula to the skin.

Cannulas and catheters are here understood to mean all kinds of "probes" as are used e.g. for introducing into and removing from vessels body fluids and can be in the form of needles, cannulas, catheters, measurement probes (e.g. for measuring certain body perameters, such as the oxygen partial pressure, etc.), as well as infusion means. Cannulas must be secured to the body, e.g. during the dialysis of patients or during longer infusions. Means for fixing cannulas and catheters are known.

EP-B1-76 896 and EP-A1-121 679 discloses a "medical dressing for fixing a probe", having a dressing portion which can be fastened to the skin and to the part of the probe projecting from the skin by means of plasters. This dressing portion is provided with a tubular extension, which serves as a support or reception means for the probe part projecting from the skin.

German utility model 82 04 827.4 describes a holding or retaining device having two clamping plates, which receive the cannula and is then secured by plaster to the skin.

DE-OS 32 12 458 discloses a bandage system for catheters to be externally applied to males and more particularly relates to the geometrical configuration of plaster strips.

German patent DE-PS 29 47 427 relates to a vein catheter bandage which, by means of a plaster with a watertight, air-permeable, pressure sensitive adhesive finished film, which can optionally have a moisture-absorbent layer on the skin-remote side, fixes a cannula with a stop valve to the skin; 95×60 mm being given as the preferred dimensions for the plaster.

DE-OS 31 05 187 describes a cannula fixing plaster with a punched out plaster segment which, after the insertion of the cannula, is fixed to the latter and in this way prevents the removal of the cannula, whilst the remaining plaster adheres to the skin.

EP-A1-116 526 relates to another principle for fastening cannulas to the skin, in which a catheter retaining device is fixed by means of a needle passed through the skin of the patient to be treated. In special cases the catheter is even sewn to the skin for fixing it into position.

For example, under the trade name POROFIX cannula plasters, plaster strips are commercially available for fixing such cannulas. They are adhesive plasters with a slit, which is in particular used for fixing Strauss cannulas during infusions.

These known cannula fixing plasters have the advantage that the underlying skin portions can breathe, the film being water vapour and oxygen-permeable, so that there can be no maceration of the skin surface.

However, it is a disadvantage of the known cannula fixing means, that the insertion or puncture point and the underlying skin portions in the puncture or insertion channel are not adequately protected against infections through bacteria which enter from the skin surface. Attempts have been made to at least partly obviate this problem by disinfecting the skin prior to puncturing. However, disinfection only covers the upper skin layers and cannot prevent the penetration of bacteria into the insertion channel from lower lying skin layers or from the outside.

It is important to ensure a good fixing of the cannula, so as to prevent slipping thereof over a long period.

The prior art arrangements only partly solve this problem. It is either necessary to use very complicated means for fixing the cannula, which are stuck to the skin with the adhesive plaster, or simple plasters with incisions or slits are used, which do not lead to a satisfactory, long-term cannula fixing.

SUMMARY OF THE INVENTION

The problem of the present invention is consequently to provide an improved cannula fixing system, which prevents the insertion or puncture point against infection, even in the case of cannulas which are left in longer, such as e.g. shunts in the case of dialysis patients and, accompanied by good fixing, simultaneously prevents damage to the skin layers.

According to the invention this problem is solved by a fixing system for fastening catheters, cannulas or the like, characterised by a skin film coated with a skin adhesion coating and having a cover film and an overplaster finished with a pressure sensitive adhesive coating adhering to the skin film and having an overplaster cover layer.

A preferred development of the invention is characterised in that the layers are superimposed in sandwich-like manner and on one side are interconnected in a partial region without an intermediate film or by an intermediate separating film, the overplaster cover layer becoming an intermediate separating film, the overplaster cover layer becoming an intermediate separating film between the skin film and the pressure sensitive adhesive coating of the overplaster.

It is also advantageous if, in a fixing system according to the invention, the skin film is a flexible, water vapour-permeable and bacteria-tight film, e.g. a natural or synthetic polymer, such as crosslinked collagen, polyurethane, etc. and as is commercially available in incision film form. The skin film and/or overplaster, as well as optionally also the pressure sensitive adhesive layers can be transparent, so as to be able to observe the insertion or puncture point.

If both the overplaster and skin film are to be made transparent, it is possible even in the case of the longer-term fixing of a cannula, catheter, etc., to constantly check the position thereof by inspecting the outside of the cannula fixing system, without it being necessary to remove or open the latter, which would have infection or injury risks for the patient. As a result of this advantageous construction, it is possible in many cases to obviate cannula changes.

If the surface of the skin film is larger than the overplaster, as a result of the larger adhesive surface a very good adhesion of the skin film to the skin is ensured and it is now possible to adhere to the skin film an overplaster with a very strong adhesive in the pressure sensitive adhesive coating, which might even lead to skin layer injuries if it was used on the skin. It is appropriate for the overplaster to have a much smaller area than the underplaster, so as to prevent any maceration of the skin by air and moisture exclusion on using an overplaster with poor air and moisture conduction.

It is advantageous in this case if the pressure sensitive adhesive layer of the overplaster more strongly adheres to the skin film than the skin adhesion layer to the skin. Preferably the overplaster cover film has a separating line and optionally two removal aids for each intermediate separating film portion.

According to a preferred development of the invention, the skin film can be coated with an active substance on one or both sides and preferably with a bactericidal substance or the like. To prevent the detachment of the edges of the skin film from the skin, in addition to the skin adhesion layer, the skin film can have an all-round, more strongly pressure sensitive adhesive adhering rim or border.

The overplaster can be perforated, so as to ensure that in the case of any necessary application of a solvent to the overplaster it is possible to ensure an easy removal thereof by neutralizing the adhesive layer by the solvent. Following said solvent treatment, it is possible to remove the upper plaster and then the cannula. The skin film can then be removed. The perforations also prevent maceration of underlying skin surfaces.

The inventive fixing system, according to a specially preferred embodiment, also includes an adhesive-forming elastic polymer or its starting material, which adheres to the skin surface and the cannula surface and following application to the skin film and insertion point forms a bacteria-tight sealing of the insertion point together with the skin film.

According to another embodiment of the invention, the inventive fixing system can also have a cannula support body and also a reception opening adapted to the outside shape of a cannula, in such a way that when the cannula support body is applied to the skin film, the cannula is fixed in a pre-determined angular position in the reception opening. The cannula support body can also have an optionally pressure sensitive adhesive finished support surface, with which it is engaged on the skin film and can e.g. be fixed during the insertion of the cannula. This embodiment is particularly advantageous if it is intended to avoid firm adhesion of the overplaster to the cannula, which could in certain circumstances be painful for the patient on removing the cannula. In this case the cannula is fastened by frictional engagement in the reception opening of the cannula support body.

Advantageously the cannula support body is a molded article from elastic material, preferably a polymer, which is optionally transparent. Silicone rubber or other polymers are e.g. suitable for this purpose.

The invention also relates to a process for the sterile fastening of a cannula to the skin, characterized by the application of a bacteria-tight skin film with skin adhesion layer to the skin in the puncture or insertion region of the cannula, passing the cannula through the skin film, applying to the skin an adhesive forming an elastic, bacteria-tight film adhering to the underplaster in the cannula insertion region, passing the cannula through the skin film, applying to the area of the underplaster surrounding the insertion point an adhesive forming an elastic, bacteria-tight film adhering to the underplaster and to at least part of the cannula portion projecting from the skin and sticking the overplaster over the cannula.

A preferred variant of the inventive process is characterized in that a cannula support body is engaged and fixed on the skin film or skin, with subsequent or prior embedding of the cannula in the reception opening of the cannula support body.

The cannula support body can be fixed in position both by means of a pressure sensitive adhesive layer, by means of an adhesive or by sticking over with the overplaster.

In a preferred embodiment of an inventive fixing system with two separate plasters comprising cover film, skin adhesion layer and skin film, together with an overplaster cover film, pressure sensitive adhesive layer and overplaster, the skin film, which is preferably an incision film, is detached from its surface cover layer and adhered to the skin surface to be provided with a cannula. The incision film is then perforated by the cannula. The punching out of an incision film portion by the hypodermic needle and the feeding of the same into the insertion or puncture channel can be obviated in that either a suitable semi-blunt cannula form is chosen, so that only a horseshoe-shaped tab is punched out and continues to be connected to the film on one side, or an incision film can be used (e.g. crosslinked collagen). Another advantageous alternative involves the use of a cannula with a retractable central pin. Easy cleaning is made possible in that prior to the introduction of liquids into the body, the inside of the cannula is cleaned e.g. by producing a vacuum on the body-remote side, sucking up of residues of punched-out portions and also tissue parts.

A particularly preferred embodiment with active ingredient-filled incision film is particularly advantageous if the inventive cannula fixing plaster is left on the skin for a long time. The same also applies in the case of patients, where an infection would have a particularly negative effect, because a cannula is frequently introduced into their vessel, e.g. in the case of dialysis patients. In such cases a so-called shunt is produced, i.e. a connection between the artery and the vein and then a new cannula can be inserted there for each dialysis. An incision film coated with bactericidal active substances on the top of the skin film, in addition or alternatively thereto, would substantially prevent a migration of bacteria towards the body-remote puncture point.

According to a particularly preferred embodiment of the inventive fixing plaster, the overplaster portion and skin film portion, separated by an intermediate separating film which is optionally adhesive on both sides, are superimposed. It is preferable for the intermediate separating film to have a separating line, which defines a larger and a smaller surface portion. It is appropriate if the removable intermediate separating film parts and cover films have removal aids.

Firstly the cover film covering the skin film on the skin side is removed (optionally using a removal aid) and the remaining sandwich-like plaster system is adhered as an entity to the skin. Subsequently part or all the overplaster is drawn off from the skin film together with the intermediate separating film. A portion of the intermediate separating film is detached from the separating intermediate film residue along a prepared separating line and detached from the overplaster. The now exposed pressure sensitive adhesive layer is adhered to the skin film. The remainder of the intermediate separating film is now flapped away from the skin film, together with the overplaster part covered but not adhered by it, so that the skin film, preferably an incision film, is located freely over the puncture point and this is then followed by puncturing. The intermediate separating film is now completely removed, optionally with a second removal aid and the overplaster is placed over the cannula, so that it rests in roughly horseshoe-shaped manner on the lower plaster and the cannula projects from the open side of the horseshoe. (Obviously the sequence of steps can be modified, e.g. the cannula is engaged first and, following this, the overplaster is stuck down.)

To avoid maceration phenomena and in order to facilitate removal of the overplaster by solvents, it may be appropriate to perforate the overplaster.

With the aid of the inventive cannula fixing plaster, the cannula is adhered in a pocket formed by the skin film and overplaster and consequently contact between cannula and skin is substantially avoided.

To avoid the punching out of a skin film portion on inserting the cannula, the latter can be engaged on one edge, even outside the fixing system, so that improved fixing of the cannula is made possible by the inventive fixing system. There is no complete covering of the insertion region by the skin film and use is solely made of the fixing action of the fixing plaster system.

The individual parts of the fixing system, such as the underplaster, overplaster, the adhesive matched thereto and the cannula support body are essential to the invention.

BRIEF DESCRIPTION OF THE DRAWINGS

The invention is described in greater detail hereinafter relative to the drawings, wherein show.

DESCRIPTION OF THE PREFERRED EMBODIMENTS

Figure 1:
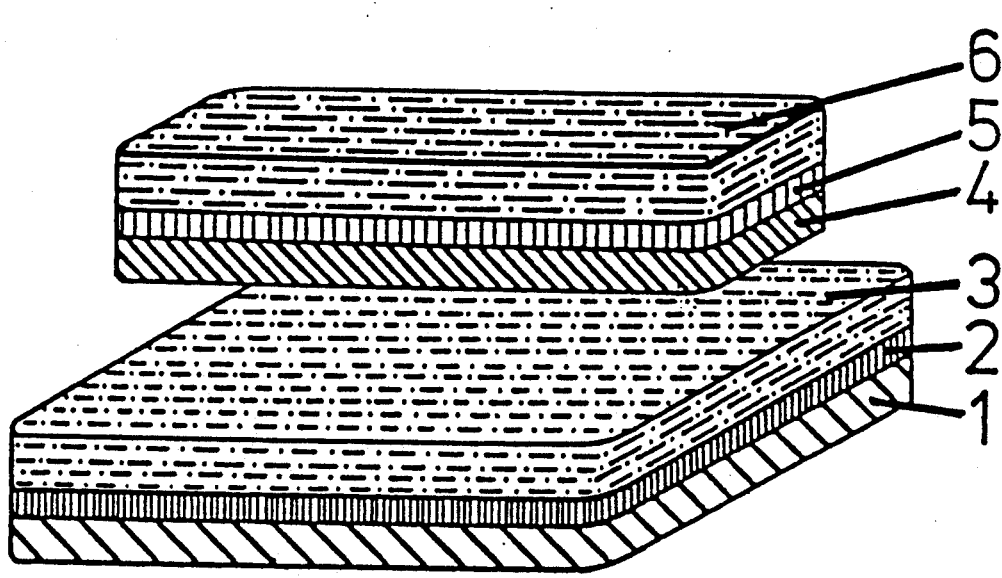
FIG. 1 an inventive system with separate overplaster and skin film.

As shown in FIG. 1, a preferred embodiment of the inventive "underplaster" comprises a cover film 1, a skin adhesion layer 2 and a skin film 3, which is preferably finished in air and watervapour-permeable and optionally also bactericidal manner. The "upper part" of the fixing system comprises an overplaster 6, a pressure sensitive adhesive layer 5 and an overplaster cover film 4, optionally with removal aid. The fixing system shown in FIG. 1 is able to fix cannula 8 which, following the adhesion of the skin film to the skin, is optionally sealed with a bacteria-tight adhesive 7 and is subsequently fastened by the overplaster 6 stuck to the skin film 3.

Figure 2:
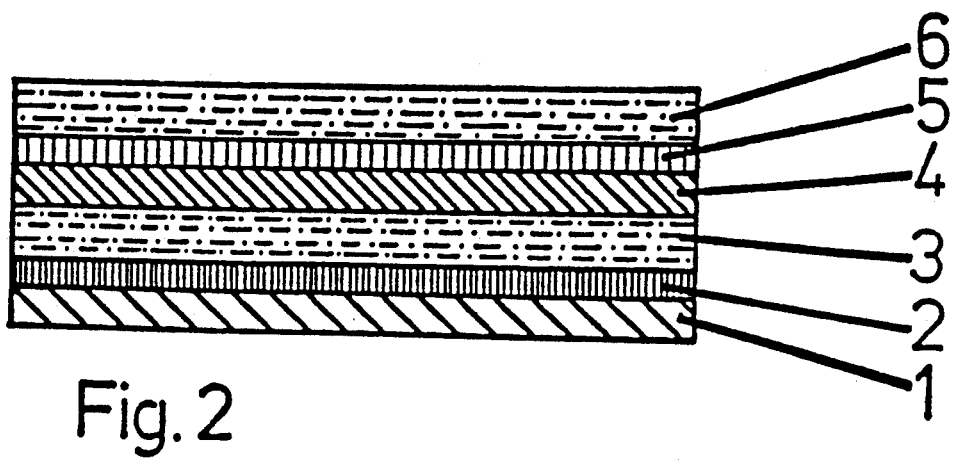
FIG. 2 a longitudinal section through a sandwich-like overplaster-skin film combination according to the invention.

FIG. 2 shows a sandwich-like variant of the inventive fixing system, in which the same layers as described in FIG. 1 are superimposed, but in this case the overplaster cover layer 4 has become an intermediate separating film.

Figure 3:
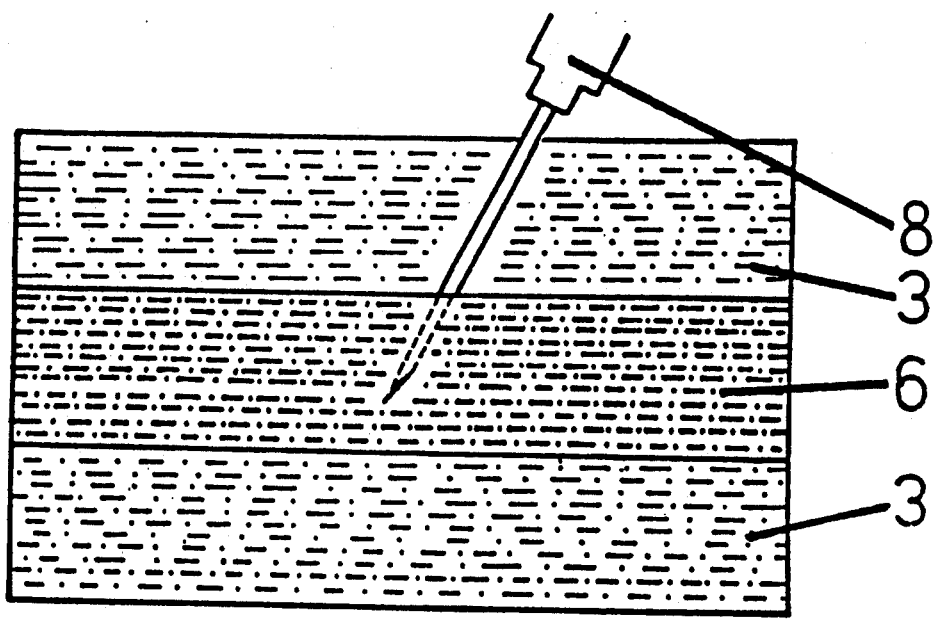
FIG. 3 a plan view of the plaster according to FIG. 2 in the fitted state.

FIG. 3 shows the plaster shown in FIG. 2 applied to the skin. A smaller overplaster 6 is stuck to a large surface skin film 2 and fixes cannula 8 in position.

Figure 4:
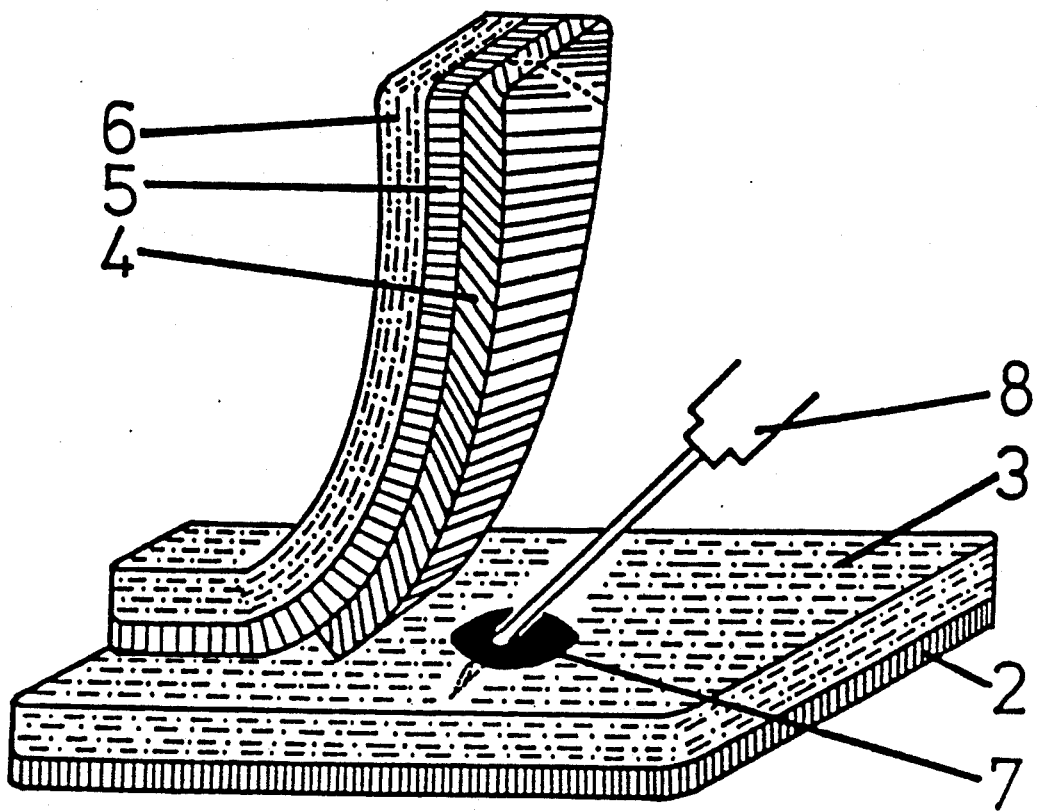
FIG. 4 the plaster according to FIGS. 2 and 3 prior to the application of the overplaster and with adhesive applied.

In FIG. 4 the cannula 8 has already perforated the stuck down skin film and the overplaster with a portion freed from the intermediate separating film has been stuck to the skin film 3. The bacteria-tight adhesive 7 has been applied around the insertion point on skin film 3 and the free cannula end, whilst forming a foil-like seal. The overplaster portion 3 still provided with the intermediate separating film 4 is flapped back and has on its end a removal aid, which facilitates the removal of the remaining intermediate film portion. The next operation is to remove by means of the removal aid the intermediate separating film 4 from the remainder of overplaster 6, to place the latter over cannula 8 and secure same by adhesion.

Figure 5:
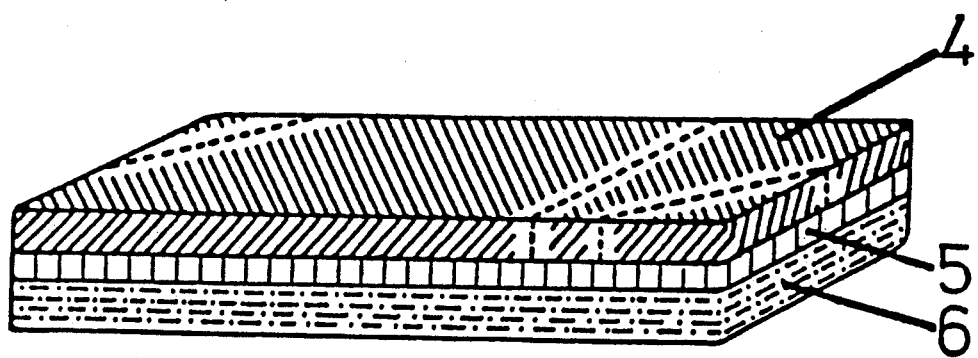
FIG. 5 a plan view of the inventive overplaster-cover layer combination with removal aid and separating line.

FIG. 5 shows the surface portion of FIG. 4 from the intermediate separating film side 3. It is possible to see two removal aids and a separating line, along which initially a part of the intermediate separating film is removed and then overplaster 6 is stuck to skin film 3.

Figure 6:
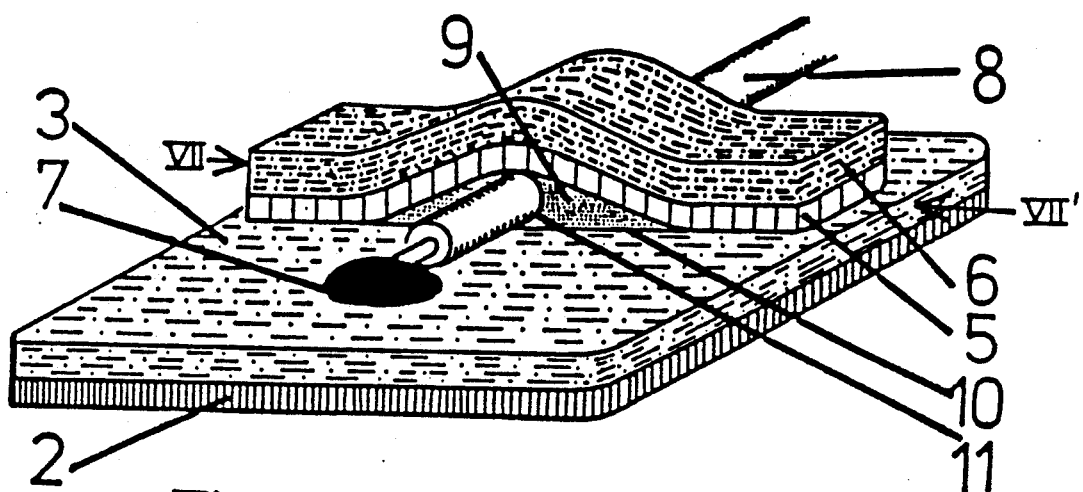
FIG. 6 a view of an inventive fixing system with cannula support body.

FIG. 6 shows a further development of the inventive fixing system, in which a cannula support body 9 formed from an elastic polymer is adhered to the skin film 3 with a support surface 10, which here has a pressure sensitive adhesive finish. The cannula support body 9 has a reception opening 11, in which the cannula 8 can be frictionally engaged. In the presently shown embodiment cannula 8 can be pressed through a slit in an elastic boundary wall of reception opening 11 and is secured by the cannula support body walls which elastically return to their inoperative position.

Figure 7:
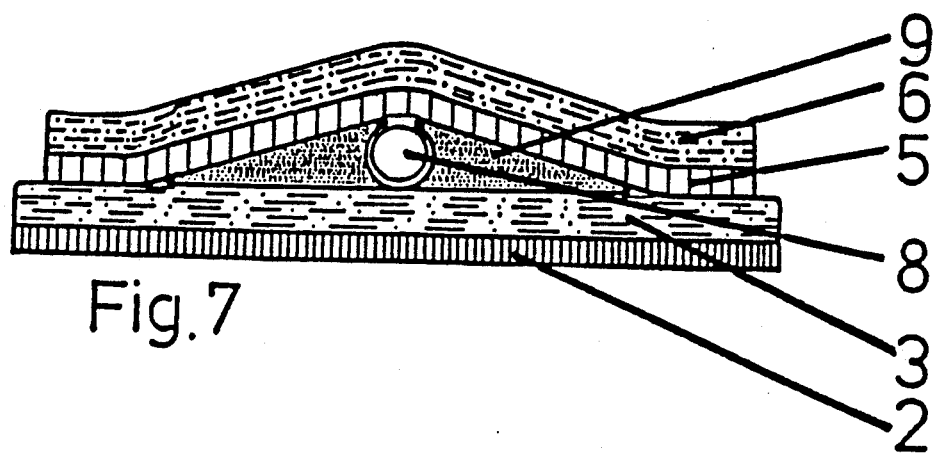
FIG. 7 the inventive fixing system of FIG. 6 along line VII-VII'.

FIG. 7 sectionally shows the fixing system of FIG. 6 along line VII—VII'. For the better fastening of cannula 8, in this case an overplaster 6 is adhered over the cannula support body 9. In this embodiment there is no need for a pressure sensitive adhesive coating of the skin support surface 10.

I claim:

1. Fixing system for sterile fastening of catheters, cannulas, needles, measurement probes and infusion means to skin surface over a skin insertion or puncture point on the skin without infection risk, comprising an underplaster including a skin film (3), and an overplaster (6) overlying the underplaster on a skin-remote face of the underplaster which further comprises the skin film (3) being coated with a skin adhesion layer (2) for adhesion to skin over such skin insertion or puncture point, the skin film having a removable cover film (1) on the skin adhesion layer, the overplaster (6) being coated with a pressure sensitive adhesive layer (5) adhering the overplaster to the skin film, the skin film (3) having an outer periphery, said skin film being imperforate within said periphery and being of flexible, water vapor-permeable and bacteria-tight film material adapted for bacteria-tight puncturing therethrough to said puncture point of a catheter needle, cannula, measurement probe or infusion means, the pressure sensitive adhesive layer having a removable overplaster cover layer (4) for overlying the skin film, the overplaster upon removal of the overplaster cover layer permitting a catheter, cannula, needle, measurement probe or infusion means to be secured between the overplaster and the skin film.

2. Fixing system according to claim 1, wherein the layers are superimposed in sandwich-like manner and are interconnected in a partial region, the overplaster cover layer (4) comprising an intermediate separating film between the skin film (3) and pressure sensitive adhesive layer (5).

3. Fixing system according to claim 2, wherein the skin film (3), overplaster (6), and the pressure sensitive adhesive layers (2) and (5) are transparent.

4. Fixing system according to claim 1, wherein the skin film (3) has a surface area which is larger than that of overplaster (6).

5. Fixing system according to claim 1, wherein the pressure sensitive adhesive layer (5) adheres more strongly to the skin film (3) than the skin adhesion layer (2).

6. Fixing system according to claim 2, characterized in that the overplaster cover layer (4) has a separating line creating two portions of different sizes.

7. Fixing system according to claim 1, wherein the skin film (3) is coated with active ingredient on at least one side constituting a bactericidal agent.

8. Fixing system according to claim 1, wherein the skin film (3) additionally has a strongly adhering adhesive border extending completely around the periphery of the skin film (3).

9. Fixing system according to claim 1, wherein the overplaster (6) is perforated.

10. Fixing system according to claim 9 wherein the skin film further includes an elastic polymer (7) which adheres to the skin film (3) and adapted to adhere to the surface of the cannula thereby forming a bacteria-tight seal for the cannula at the skin point.

11. Fixing system according to claim 1 in combination with a cannula support body (9) having a case with a support surface contacting said skin film, with a pressure sensitive adhesive being coated on said support surface (10) and with a reception opening (11) adapted to the external shape of a cannula (8), such cannula (8) in the case of the cannula support body (9) being applied to the skin film (3) such that cannula (8) is fixed in a predetermined angular position in reception opening (11).

12. Fixing system according to claim 11, wherein the cannula support body (9) is a molded article made from a transparent elastic polymer.

13. A fixing system according to claim 1, wherein the skin film (3) is only perforated to the extent permitting the insertion therethrough of the catheter, needle, cannula, measurement probe or infusion means to the puncture point.

14. A fixing system according to claim 13, wherein the skin film further includes an elastic polymer (7) forming an adhesive adhering to the skin film (3) and adapted to adhere to the surface of the catheter, needle, cannula, measurement probe or infusion means forming a bacteria-tight seal.

15. Fixing system according to claim 10, wherein the elastic polymer (7) forms an adhesive which adheres to the skin film (3) and surface of the cannula thereby forming a bacteria-tight seal for the cannula at the skin point.

16. Fixing system according to claim 1, further comprising said skin film being the synthetic polymer polyurethane.

17. Process for the sterile fastening of a cannula to the skin, comprising applying a bacteria-tight skin film having a skin adhesion layer to the skin so as to define a cannula insertion region, puncturing the skin film with the cannula at a skin puncture point, the skin film (3) being a flexible, water vapor-permeable and bacteria-tight film material, applying an overplaster having an adhesive forming an elastic, bacterial-tight film adhering to the skin film in a cannula insertion region surrounding the puncture point, at least part of the cannula projecting from the skin, so that the cannula insertion puncture region is sealed, then sticking the overplaster over the cannula part projecting from the skin film.

18. Process according to claim 17, further comprising securing a cannula support body to the skin film, and embedding of the cannula in a reception opening of the cannula support body.

19. Fixing system for sterile fastening of catheters, cannulas, needles, measurement probes and infusion means to skin surface over a skin insertion or puncture point on the skin without infection risk, comprising an underplaster including a skin film (3), and an overplaster (6) overlying the underplaster on a skin-remote face of the underplaster which further comprises the skin film (3) being coated with a skin adhesion layer (2) for adhesion to skin over such skin insertion or puncture point, the skin film having a removable cover film (1) on the skin adhesion layer, the overplaster (6) being coated with a pressure sensitive adhesive layer (5) adhering the overplaster to the skin film, the skin film (3) having an outer periphery, said skin film being imperforate within said periphery and being of flexible, water-vapor permeable and bacteria-tight film material adapted for bacteria-tight insertion therethrough to said puncture point of a catheter, needle, cannula, measurement probe or infusion means, said insertion made by puncturing said skin film (3), the pressure-sensitive adhesive layer having a removable overplaster cover layer (4) for overlying the skin film, the overplaster upon removal of the overplaster cover layer permitting a catheter, cannula, needle, measurement probe or infusion means to be secured between the overplaster and the skin film (3), the skin film (3), overplaster (6) and the adhesive layers (2) and (5) being transparent.

20. A fixing system according to claim 19, wherein the skin film (3) is only perforated to the extent permitting the insertion therethrough of the catheter, needle, cannula, measurement probe or infusion means to the puncture point.

* * * * *